United States Patent
Driemel

(10) Patent No.: US 8,294,460 B2
(45) Date of Patent: Oct. 23, 2012

(54) LOCAL COIL ARRANGEMENT FOR MAGNETIC RESONANCE APPLICATIONS AND PATIENT BED FOR A MAGNETIC RESONANCE SYSTEM, WITH INTEGRATED ELECTRICAL INTERFACES

(75) Inventor: Daniel Driemel, Oederan (DE)

(73) Assignee: Siemens Aktiengesellschaft, Munich (DE)

( * ) Notice: Subject to any disclaimer, the term of this patent is extended or adjusted under 35 U.S.C. 154(b) by 405 days.

(21) Appl. No.: 12/641,567

(22) Filed: Dec. 18, 2009

(65) Prior Publication Data
US 2010/0156420 A1    Jun. 24, 2010

(30) Foreign Application Priority Data
Dec. 18, 2008 (DE) .................. 10 2008 063 629

(51) Int. Cl.
*G01V 3/00* (2006.01)

(52) U.S. Cl. ..................................... 324/307

(58) Field of Classification Search .......... 324/300–322; 600/410–435
See application file for complete search history.

(56) References Cited

U.S. PATENT DOCUMENTS

| | | | | |
|---|---|---|---|---|
| 5,197,474 A * | 3/1993 | Englund et al. | ............... | 600/415 |
| 5,261,403 A * | 11/1993 | Saito et al. | ..................... | 600/422 |
| 5,952,830 A * | 9/1999 | Petropoulos et al. | ......... | 324/318 |
| 6,029,082 A * | 2/2000 | Srinivasan et al. | ............. | 600/422 |
| 6,529,004 B1 * | 3/2003 | Young | ........................... | 324/318 |
| 6,791,327 B2 * | 9/2004 | Skloss | ........................... | 324/318 |
| 7,446,531 B2 * | 11/2008 | Schnell et al. | ................. | 324/318 |
| 7,602,189 B2 * | 10/2009 | Decke et al. | ................... | 324/318 |
| 7,701,209 B1 * | 4/2010 | Green | ........................... | 324/307 |
| 7,714,582 B2 * | 5/2010 | Hagen et al. | ................... | 324/322 |
| 7,722,375 B2 * | 5/2010 | Hagen et al. | ................... | 439/310 |
| 7,844,318 B2 * | 11/2010 | Rezzonico et al. | ............ | 600/410 |
| 7,869,858 B2 * | 1/2011 | Calderon et al. | .............. | 600/415 |
| 7,884,607 B2 * | 2/2011 | Kundner et al. | .............. | 324/318 |
| 7,940,047 B2 * | 5/2011 | Hansen et al. | ................. | 324/322 |
| 8,055,326 B1 * | 11/2011 | Dworkin et al. | .............. | 600/422 |
| 8,131,341 B2 * | 3/2012 | Heumann et al. | ............. | 600/415 |
| 2005/0060047 A1 | 3/2005 | Schor | | |
| 2007/0016003 A1 | 1/2007 | Piron et al. | | |
| 2007/0282192 A1 | 12/2007 | Rezzonico et al. | | |
| 2008/0030195 A1 * | 2/2008 | Hagen et al. | ................... | 324/322 |

* cited by examiner

*Primary Examiner* — Dixomara Vargas
(74) *Attorney, Agent, or Firm* — Schiff Hardin LLP

(57) ABSTRACT

A local coil arrangement for magnetic resonance applications has a mechanically dimensionally stable support element that rests on a patient bed so as to transfer the weight of the local coil arrangement to the patient bed. The local coil arrangement has at least one local coil to excite and/or to receive magnetic resonance signals and a multipole, prefabricated electrical interface via which the local coil can be electrically contacted. The electrical interface is arranged so as to be dimensionally stable at the support element. Positioning aids for positioning of local coil arrangement are arranged on the support surface that also transfer the weight of the local coil arrangement is transferred to the patient bed as well as plugging the electrical interface into an electrical counter-interface.

11 Claims, 4 Drawing Sheets

LOCAL COIL ARRANGEMENT FOR MAGNETIC RESONANCE APPLICATIONS AND PATIENT BED FOR A MAGNETIC RESONANCE SYSTEM, WITH INTEGRATED ELECTRICAL INTERFACES

BACKGROUND OF THE INVENTION

1. Field of the Invention

The present invention concerns a local coil arrangement as well as a patient bed for a magnetic resonance apparatus.

2. Description of the Prior Art

Local coil arrangements for magnetic resonance applications are known that have a mechanically dimensionally stable supporting element with which the local coil arrangement is placed on a patient bed of a magnetic resonance system in operation, that in this state transfers the weight of the local coil arrangement to the patient bed, and wherein the local coil arrangement has at least one local coil to excite and/or to receive magnetic resonance signals, an a multipole, prefabricated electrical interface with which the local coil can be electrically contacted.

Patient bed for magnetic resonance systems are known that have a surface to support a patient, positioning aids to position a local coil arrangement for magnetic resonance applications arranged on the support surface, a multipole, prefabricated electrical counter-interface arranged in a mechanically dimensionally stable manner at the patient bed, wherein the weight of the local coil arrangement is transferred to the patient bed by suitable positioning of the mechanically dimensionally stable supporting element of a known local coil arrangement on the supporting surface.

Among local coil arrangements, head coil arrangements and neck coil arrangements represent the best known examples.

Conventionally, (at least) one electrical interface of the local coil arrangement is attached to a flexible cable. The corresponding electrical counter-interface is arranged at the side on the patient bed. To electrically connect the local coil arrangement with the patient bed, the electrical interface is connected with the electrical counter-interface in a separate operation that is different from the positioning of the local coil arrangement on the patient bed.

This conventional procedure exhibits a number of disadvantages.

For example, the separate operation is required for each interface. Working time is required for the execution of the operation. Moreover, the operation is prone to error, for example, it can be forgotten. The disadvantage that separate operations are required is particularly severe if the local coil arrangement has multiple prefabricated electrical interfaces.

Furthermore, the electrical interface as such is exposed to mechanical stresses. For example, the housing of the electrical interface can be struck in the handling of the local coil arrangement and during its transport. Such impact can lead to a fracture of the housing of the electrical interface, for example.

The cables are also relatively sensitive, for example with regard to crushing.

Lastly, contacts can be bent and disfigured by improper handling of the electrical interface in the connecting with the electrical counter-interface.

SUMMARY OF THE INVENTION

An object of the present invention is to provide a local coil arrangement and a patient bed with which the aforementioned problems can no longer occur.

According to the invention, a local coil arrangement of the aforementioned type is designed with the electrical interface arranged so as to be dimensionally stable at the supporting element so that the electrical interface can be mechanically and electrically plugged in by suitable positioning of the supporting element on the patient bed with an electrical counter-interface that is arranged so as to be dimensionally stable at the patient bed.

Also according to the invention, corresponding to this a patient bed of the aforementioned type is designed such that the electrical counter-interface is arranged in the region of the positioning aids so that, in addition to transferring the weight of the local coil arrangement, a dimensionally stable electrical interface arranged on the supporting surface can be mechanically and electrically plugged into the electrical counter-interface by the positioning of the supporting element.

In a preferred embodiment of the local coil arrangement, in the state in which the local coil arrangement rests on the patient bed, the supporting element has an underside facing toward the patient bed, and the electrical interface is arranged on the underside. This embodiment mechanically protects the electrical interface and the electrical counter-interface in the state in which the local coil arrangement rests on the patient bed.

In a further preferred embodiment of the local coil arrangement, in the state in which the local coil arrangement rests on the patient bed, the supporting element rests with the electrical interface and precisely two additional supporting points on the patient bed so that the electrical interface and the two additional supporting points form a three-point support of the local coil arrangement on the patient bed. This embodiment causes the local coil arrangement to be stably supported on the patient bed. Tilting or shaking is not possible.

In a further preferred embodiment of the local coil arrangement, the electrical interface is connected with the electrical counter-interface by insertion in a plug-in direction, and the plug-in direction is notably angled both relative to a support plane defined by the patient bed and relative to a normal direction orthogonal to the support plane. The term "clearly angled" means that an angle that the plug direction forms with the support plane or the normal direction is at least 20°. An angle is preferably at least 30°, in particular 40° or 50°.

In a preferred embodiment of the patient bed the electrical interface is connected with the electrical counter-interface by insertion in a plug-in direction, and the plug-in direction is notably angled both relative to the support surface and relative to a normal direction orthogonal to the supporting surface. The above definition of the term "notably angled" applies to this embodiment as well.

In a further preferred embodiment of the local coil arrangement, in the state in which the local coil arrangement rests on the patient bed, the electrical interface is elevated relative to a region of the patient bed that surrounds it. The same applies for the electrical counter-interface of the patient bed.

The last cited embodiment of the local coil arrangement is particularly advantageous when the electrical interface is arranged in a recess of the patient bed in the state in which the local coil arrangement rests on the patient bed. Corresponding to this, in this case the electrical counter-interface is arranged in a recess of the patient bed relative to said patient bed.

In a preferred embodiment of the patient bed according to the invention the electrical counter-interface is covered by a cover as viewed in a normal direction orthogonal to the supporting surface. It is thereby achieved that the electrical counter-interface is better protected from gradual contamination by dust and the like.

DESCRIPTION OF THE PREFERRED EMBODIMENTS

Figure 1:
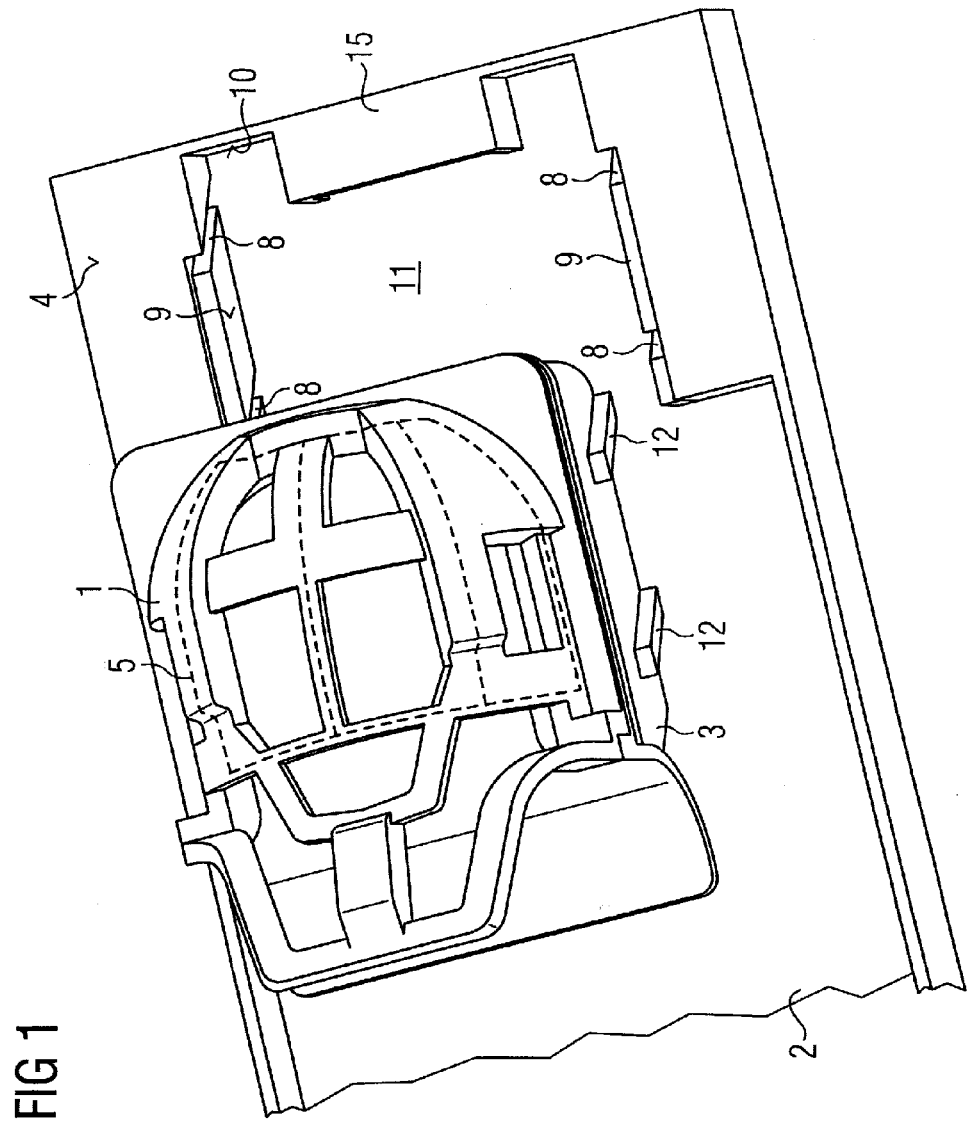
FIGS. 1 through 4 show perspective views of an embodiment of a local coil arrangement and a patient bed in accordance with the invention.
Figure 2:
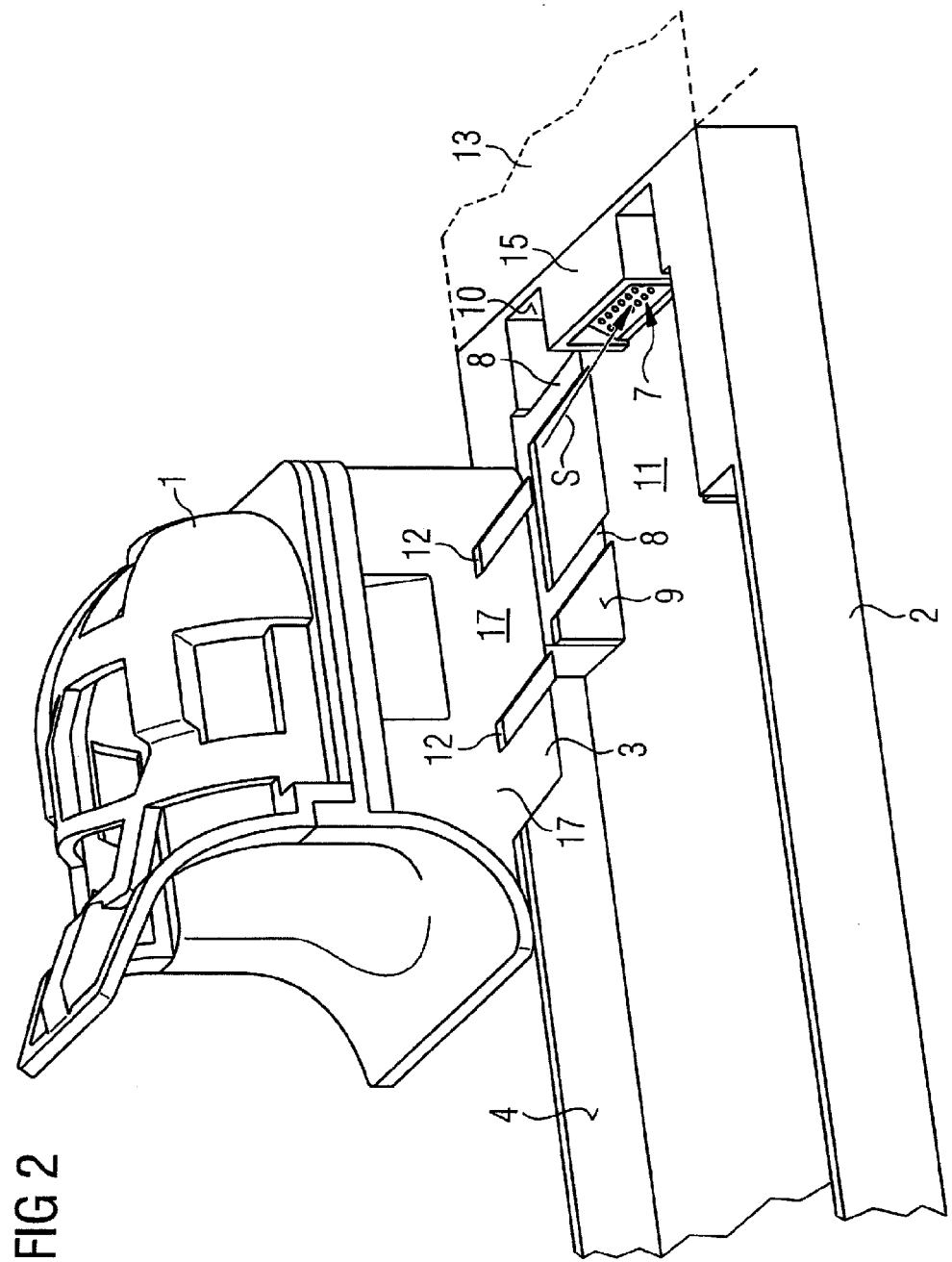
Figure 3:
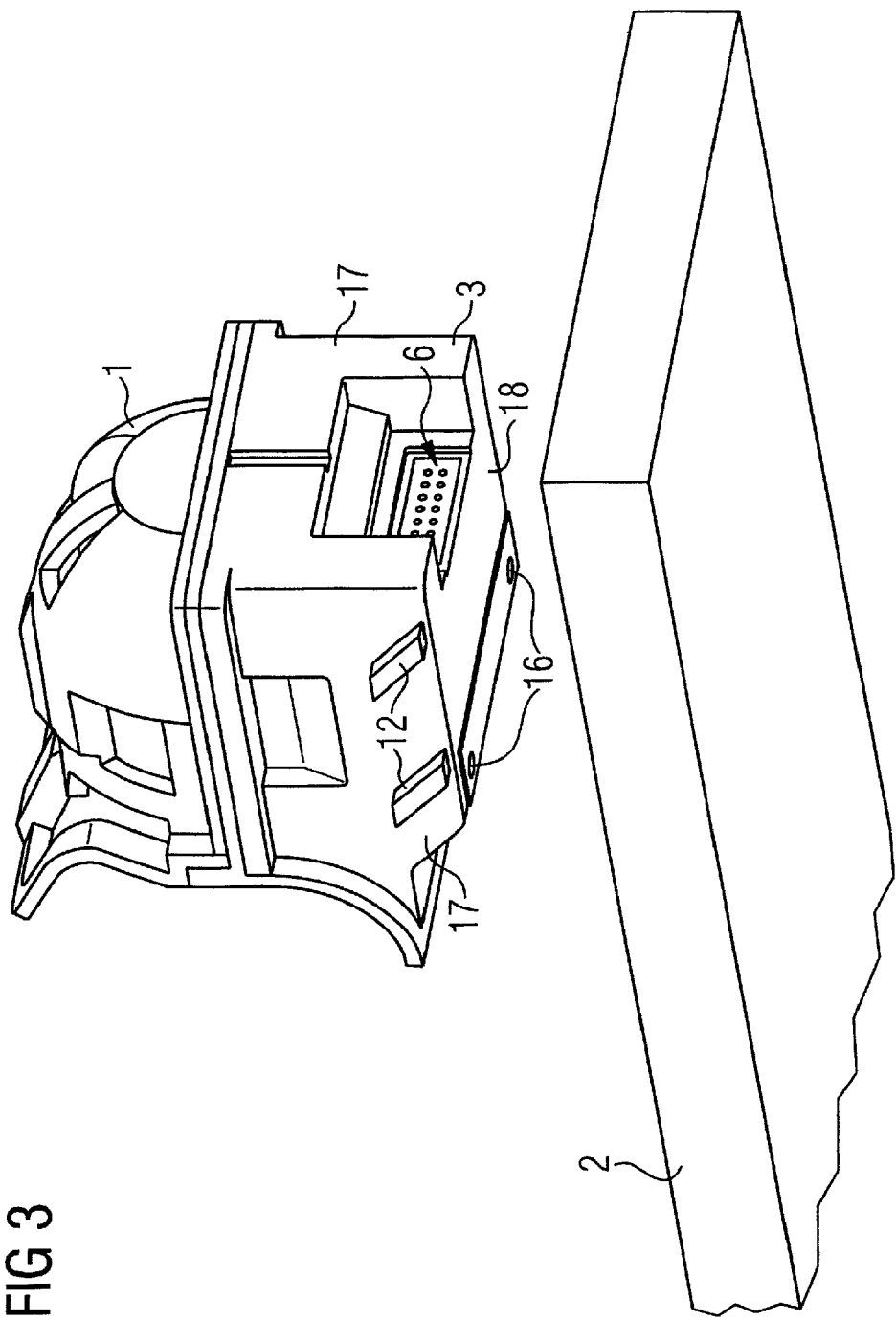
Figure 4:
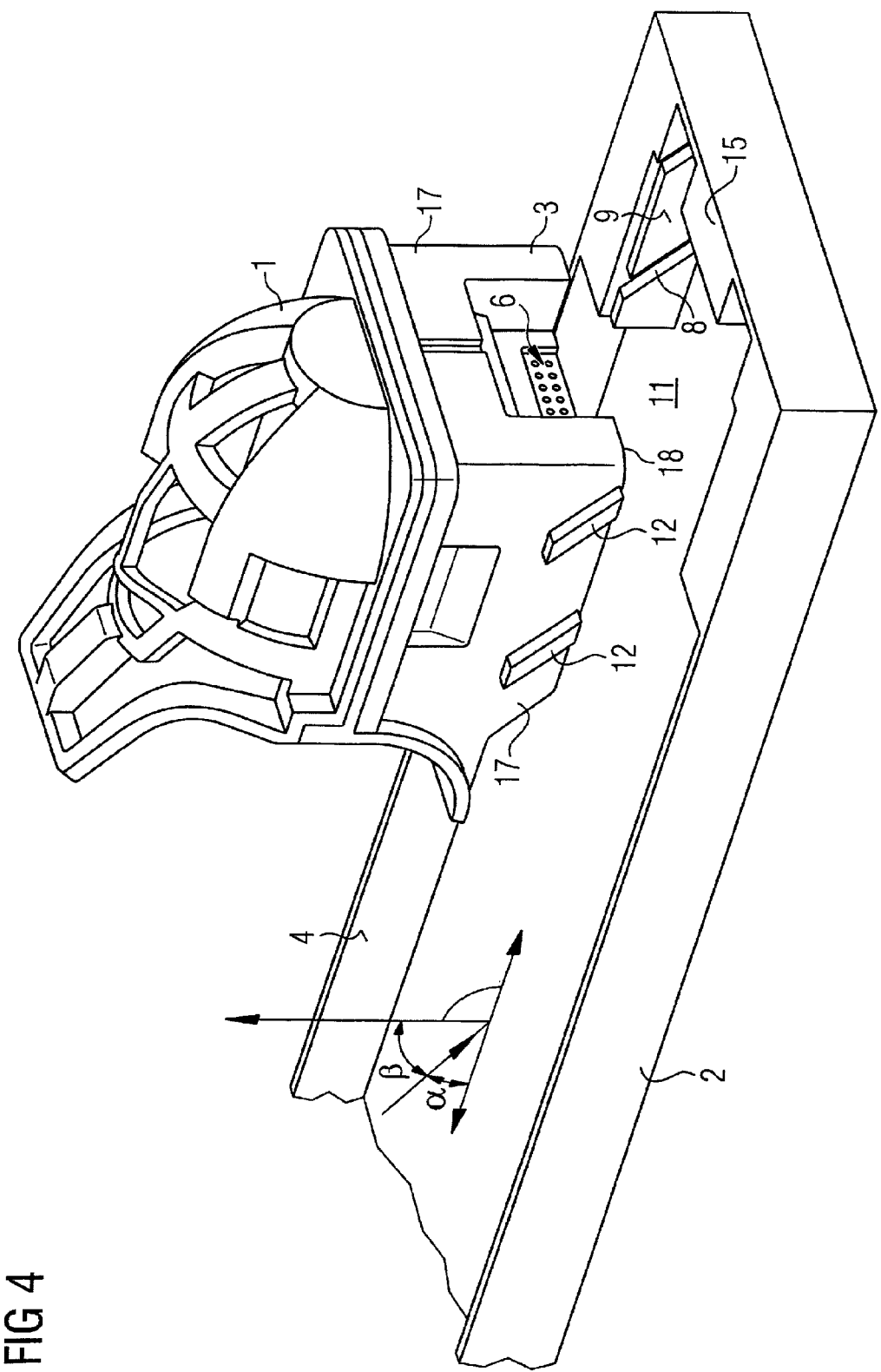

FIGS. 1 through 4 schematically show a local coil arrangement 1 for magnetic resonance applications and a patient bed 2 for a magnetic resonance system. FIGS. 1 through 4 show the same local coil arrangement 1 and the same patient bed 2. Only the perspective from which the depiction occurs is respectively different from FIG. 1 through FIG. 4. FIGS. 1 through 4 are therefore explained together in the following.

The local coil arrangement 1 is fashioned as a head coil arrangement according to FIGS. 1 through 4. However, this embodiment is only an example. The local coil arrangement 1 could likewise be fashioned as a chest coil arrangement, as an ankle coil arrangement, as a knee coil arrangement etc. for example.

The local coil arrangement 1 has a mechanically dimensionally stable supporting element 3. The supporting element 3 is that element of the local coil arrangement 1 with which the local coil arrangement 1 rests on the patient bed 2 in operation and which in this state transfers the weight of the local coil arrangement 1 to the patient bed 2. For this purpose the patient bed 2 has a support surface 4. The support surface 4 is that element of the patient bed 2 on which a patient (not shown in FIG. 1 through 4) rests.

The supporting element 3 is mechanically dimensionally stable. Among other things, the term "mechanically dimensionally stable" encompasses "mechanically rigid", but the term is not limited in this way. It is important that the supporting element 3 is either rigid or is flexible only to a slight extent. For example, a flexibility within the range of at maximum one to two millimeters can be allowable by provision of corresponding elastic components.

The local coil arrangement 1 has at least one local coil 5. The ferrules and the antenna rods of an antenna structure similar to a birdcage are shown purely as examples in dashed lines in FIG. 1, but the local coil 5 could be fashioned differently.

The local coil 5 normally serves to receive magnetic resonance signals. In the individual case, it is also possible that magnetic resonance signals are excited by means of the local coil 5.

In the operation of the local coil arrangement 1, the local coil 5 must be electrically connected with a control and evaluation device. The control and evaluation device is not the subject matter of the present invention and therefore is not shown in the figures.

To connect the local coil 5 with control and evaluation device, the local coil arrangement 1 possesses a multipole, prefabricated electrical interface 6. The electrical interface 6 is permanently connected with the local coil 5 within the local coil arrangement 1. The local coil 5 can be electrically contacted from outside the local coil arrangement 1 via the electrical interface 6.

In the prior at, and also within the scope of the present invention, the control and evaluation device is permanently connected with a prefabricated, multipole electrical counter-interface 7. The electrical counter-interface 7 is arranged in a mechanically dimensionally stable manner at the patient bed 2, both in the prior art and within the scope of the present invention.

In the prior art and also in the present invention, positioning aids 8 are arranged on the support surface 4. The positioning aids 8 serve for the positioning of the local coil arrangement 1.

In the simplest case, the positioning aids 8 can simply be the side surfaces 9 and the facing surface 10 of a recess 11 of the patient bed 2. In this case, the local coil arrangement 1 could be placed with its supporting element 3 on the patient bed 2 so that it initially exhibits a defined elevation. The supporting element 3 could then be directed between the side surfaces 9 so that the local coil arrangement 1 is also positioned in the lateral direction. By displacement of the local coil arrangement 1 up to the facing surface 10, in this case the local coil arrangement 1 could be positioned at a defined position relative to the patient bed 2. Other embodiments that are not shown in FIGS and are not described in the following are also likewise possible.

As shown, the positioning aids 8 are fashioned as linear guides (for example as guide rails). The positioning aids 8 interact with corresponding counter-elements 12 (for example corresponding guide recesses) that are arranged at the supporting element 3. Via such an embodiment it is achieved that the supporting element 3 is already directed relative to the patient bed 2 before reaching its end position, such that the supporting element 3 has only a single degree of freedom relative to the patient bed 2. The degree of freedom is preferably a translational degree of freedom, corresponding to the depiction in FIGS. 1 through 4. Alternatively, it would be possible to realize a rotational degree of freedom (keyword "pivot movement") or a different degree of freedom (for example similar to a link direction).

Independent of the precise embodiment of the positioning aids 8, via the positioning aids 8 cause the supporting element 3, and with it the local coil arrangement 1 in its entirety, are positioned in a predetermined position relative to the patient bed 2. In the positioned state, the weight of the local coil arrangement 1 is transferred to the patient bed 2.

According to the invention, the electrical interface 6 is arranged so as to be dimensionally stable at the supporting element 3. Furthermore, according to the invention the electrical counter-interface 7 is arranged in the region of the positioning aids 8. The arrangement of the electrical interface 6 at the supporting element 3 and the arrangement of the electrical counter-interface 7 at the patient bed 2 are matched to one another such that the electrical interface 6 is mechanically and electrically plugged in by the positioning of the supporting element 3 on the patient bed 2 with the electrical counter-interface 7. With the corresponding arrangement of the electrical interface 6 and the electrical counter-interface 7, it is thus achieved that not only the weight of the local coil arrangement 1 is transferred to the patient bed 2 by the positioning of the supporting element 3 on the support surface 4; but also the electrical interface 6 is mechanically and electrically connected with the electrical counter-interface 7.

The translational degree of freedom shown in FIGS. 1-4 (=plug direction S) in the positioning of the local coil arrangement 1 can in principle proceed in an arbitrary direction. In particular, the degree of freedom can run parallel to a support plane 13 defined by the patient bed 2. The support plane 13 is essentially defined by the plane of the support surface 4. The plug direction S could likewise run at an arbitrary angle relative to the support plane 13, in the extreme case in a normal direction 13 orthogonal to the support plane 13. However, it is preferred that the plug direction S is clearly angled both relative to the support plane 13 or the support surface 4 and relative to the normal direction 14. An angle α of the plug direction S relative to the support plane 13 should advantageously be between 20° and 70°. It is preferred when the angle α is between 30° and 60°. It is particularly preferred when the angle α is between 40° and 50°, thus for instance in a range of the angle bisectors between the support plane 13 and the normal direction 14. An angle β of the plug direction S relative to the normal direction 13 always results in 90°-α.

The preferred selection of the plug direction S explained in the preceding is advantageous both at an orientation parallel to the support plane 13 and relative to an orientation orthogonal to the support plane 13. With regard to an orientation parallel or, respectively, nearly parallel to the support plane 13, the advantage exists that the weight of the local coil arrangement 1 possesses a component that is directed in the direction of the plug direction S. Due to its weight the local coil arrangement 1 thus assists the electrical interface 6 in remaining in the plugged-in (state) with respect to the electrical counter-interface 7. In particular, accidental detachment of the electrical interface 6 from the electrical counter-interface 7 is nearly impossible.

The orientation orthogonal or nearly orthogonal to the support plane 13 provides the advantage that—given an angled course of the plug direction S—it is possible to provide a cover 15 which covers the electrical counter-interface 7 as viewed in the normal direction 14. The danger of a contamination of contacts of the electrical counter-interface 7 can therefore be markedly reduced.

According to FIGS. 1 through 4, it is furthermore preferred that, in the state in which the local coil arrangement 1 rests on the patient bed 2, the supporting element 3 rests with the electrical interface 6 and with precisely two supporting points 16 on the patient bed 2. Moreover, the local coil arrangement 1 is spaced from the patient bed 2. With this embodiment, the electrical interface 6 and the two supporting points 16 form a three-point support of the local coil arrangement 1 on the patient bed 2. A stable support of the local coil arrangement 1 on the patient bed 2 that is free of play results.

Furthermore, it is preferred for the electrical counter-interface 7 to be arranged elevated relative to a surrounding region 17 of the patient bed 2. Corresponding to this, in the state in which the local coil arrangement 1 rests on the patient bed 2 the electrical interface 6 is likewise arranged elevated relative to the region 17. In this case a danger that bodily fluids (sweat, urine, gastric juices, . . . ) can reach into the electrically sensitive region of the electrical interface 6 and the electrical counter-interface 7 is markedly reduced.

Furthermore, it is preferred for the electrical counter-interface 7 to be arranged in the recess 10. Corresponding to this, the electrical interface 6 is also arranged in the recess 10 in the state in which the local coil arrangement 1 rests on the patient bed 2.

It is possible that the electrical interface 6 is arranged in a side region 17 of the supporting element 3. However, the electrical interface 6 is advantageously arranged on an underside 18 of the supporting element 3. The underside 18 is that side of the supporting element 3 which faces towards the patient bed 2 in the state in which the local coil arrangement 1 rests on the patient bed 2.

A number of modifications of the principles explained in the preceding are possible. For example, a signal of an optical and/or acoustic nature can be triggered via a contact pair of the electrical interface 6 and the electrical counter-interface 7 in order to indicate a correct plugging of the electrical interface 6 into the electrical counter-interface 7. It is also possible to generate an acoustic click noise via a latching mechanism. Furthermore, it is possible to attach corresponding arm devices to apply high plugging or detaching forces and/or in particular to assist the unplugging procedure via ejectors or compression springs. Latching mechanisms can also be provided for fixing. In particular, such a latching mechanism is reasonable given a course of the plug direction S that is parallel to the support plane 13. It is also possible to provide a cover, in particular for the electrical counter-interface 7 (possibly also for the electrical interface 6). In particular given a perpendicular plugging, such a cover is reasonable for the electrical counter-interface. The covers can alternatively be opened manually before the placement of the local coil arrangement 1 or even automatically upon placement of the local coil arrangement and thus uncover the respective interface 6, 7.

The present invention has many advantages. No external conductor to the local coil arrangement 1 is required. The greater the angle α, the greater the extent to which the local coil arrangement 1 assists the plugging process and the plugged-in state via its weight. Given a more inclined plugging, the realizable guide length increases inversely with a plug direction that essentially runs in the normal direction 14. A fixing with locking and unlocking mechanism can be omitted in many cases. In particular, the angled plugging offers the advantage to assist the natural movement direction of the user in the positioning of the local coil arrangement 1 on the patient bed 2 and in the removal of the local coil arrangement from the patient bed 2.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance local coil assembly comprising:
 a magnetic resonance local coil configured to at least to receive magnetic resonance signals from an examination subject on a patient bed in a magnetic resonance apparatus, said patient bed defining a supporting plane;
 a mechanically dimensionally stable supporting element, in which said local coil is mounted, configured for placement on said supporting plane of the patient bed to transfer weight of the local coil to the patient bed, said supporting element being configured to conform to a body part of the examination subject;
 a multipole, prefabricated electrical interface mounted in said supporting element and electrically connected to the local coil in said supporting element; and
 said electrical interface being dimensionally stably mounted in said supporting element and being configured to mate, by insertion in a plug-in direction, with an electrical counter-interface that is dimensionally stably mounted to said patient bed, with said plug-in direction oriented at an angle of at least 20° relative to said supporting plane and at an angle relative to the surface normal of said supporting plane that is equal to 90° minus said angle relative to said supporting plane, and said supporting element being configured to simultaneously mechanically hold said local coil on said patient bed and place said electrical interface and said electrical counter-interface in mating, electrical connection with each other.

2. A local coil assembly as claimed in claim 1 wherein said supporting element comprises an underside configured to face toward said patient bed when said supporting element is placed on said patient bed, and wherein said electrical interface is mounted at said underside of said supporting element.

3. A local coil assembly as claimed in claim 1 wherein said supporting element comprises exactly two supporting points with which said supporting element contacts said patient bed when said supporting element is placed on said patient bed, said two supporting points and said electrical interface forming a three-point support for said supporting element and said local coil on said patient bed.

4. A local coil assembly as claimed in claim 1 wherein said electrical interface is mounted in said supporting element at a location and with an orientation that causes said electrical interface to be elevated with respect to a region of said patient bed surrounding said supporting element when said supporting element is placed on said patient bed.

5. A local coil assembly as claimed in claim 4 wherein said electrical interface is mounted in said supporting element at a position and orientation that causes said electrical interface to be located in a recess of the patient bed when said supporting element is placed on said patient bed.

6. A patient bed assembly for a magnetic resonance system, comprising:
   a patient bed having a supporting surface configured to support a patient thereon in a magnetic resonance system, said patient bed defining a supporting plane;
   said patient bed comprising mechanical positioning aids configured to position a local coil assembly for receiving magnetic resonance signals on said supporting surface with respect to said supporting plane;
   a multipole, prefabricated electrical counter-interface that is mechanically dimensionally stably mounted in said patient bed in proximity to said positioning aids;
   said positioning aids being configured to cause weight of said local coil assembly to be transferred to said patient bed by positioning of said local coil assembly on said supporting surface with said positioning aids while simultaneously making mechanical and electrical connection between said electrical counter-interface and an electrical interface of said local coil assembly; and
   said electrical interface being configured for mating and electrical connection with said electrical counter-interface by insertion in a plug-in direction, and said electrical counter-interface being configured with said plug-in direction oriented at an angle of at least 20° relative to said supporting plane and at an angle relative to the surface normal of said supporting plane that is equal to 90° minus said angle relative to said supporting plane.

7. A patient bed assembly as claimed in claim 6 wherein said electrical interface is configured for mating and electrical connection with said electrical counter-interface by insertion in a plug-in direction, and wherein said patient bed defines a supporting plane on which said supporting element is supported when said supporting element is placed on said patient bed, said electrical counter-interface being configured with said plug-in direction oriented at an angle of at least 20° relative to said support plane and at an angle relative to the surface normal of said support plane that is equal to 90° minus said angle relative to said support plane.

8. A patient bed assembly as claimed in claim 6 wherein said electrical counter-interface is mounted at a position that is elevated relative to surrounding region of said patient bed.

9. A patient bed assembly as claimed in claim 8 wherein said patient bed has a recess and wherein said electrical counter-interface is mounted in said recess.

10. A patient bed assembly as claimed in claim 6 wherein said patient bed defines a supporting surface configured to allow placement of said local coil assembly thereon, and comprising a cover that covers said electrical counter-interface as seen in a direction corresponding to a surface normal of said supporting surface.

11. A magnetic resonance local coil and patient bed assembly, comprising:
   a patient bed configured to receive an examination subject thereon in a magnetic resonance apparatus, said patient bed comprising positioning aids and an electrical counter-electrode that is dimensionally stably mounted to said patient bed, said patient bed defining a supporting plane; and
   a local coil assembly comprising a magnetic resonance local coil configured to at least to receive magnetic resonance signals from an examination subject on the patient bed in the magnetic resonance apparatus, a mechanically dimensionally stable supporting element, in which said local coil is mounted, configured for placement on said supporting plane of the patient bed by interaction with said positioning aids to transfer weight of the local coil to the patient bed, said supporting element being configured to conform to a body part of the examination subject, a multipole, prefabricated electrical interface mounted in said supporting element and electrically connected to the local coil in said supporting element, and said electrical interface being dimensionally stably mounted in said supporting element and being configured to mate, by insertion in a plug-in direction, with said electrical counter-interface, said supporting element and said positioning aids being configured to simultaneously mechanically hold said local coil on said patient bed and place said electrical interface and said electrical counter-interface in mating, electrical connection with each other, and with said plug-in direction oriented at an angle of at least 20° relative to said supporting plane and at an angle relative to the surface normal of said supporting plane that is equal to 90° minus said angle relative to said supporting plane.

* * * * *